(12) United States Patent
Heffernan

(10) Patent No.: US 10,119,847 B2
(45) Date of Patent: Nov. 6, 2018

(54) INTERIOR SENSOR WITH A REMOTE POWER SOURCE

(71) Applicant: Alfred Heffernan, Stow, MA (US)

(72) Inventor: Alfred Heffernan, Stow, MA (US)

( * ) Notice: Subject to any disclaimer, the term of this patent is extended or adjusted under 35 U.S.C. 154(b) by 274 days.

(21) Appl. No.: 14/958,342

(22) Filed: Dec. 3, 2015

(65) Prior Publication Data

US 2016/0161298 A1 Jun. 9, 2016

Related U.S. Application Data

(60) Provisional application No. 62/089,317, filed on Dec. 9, 2014.

(51) Int. Cl.
| | |
|---|---|
| *G08B 17/10* | (2006.01) |
| *G01D 11/24* | (2006.01) |
| *G01N 33/00* | (2006.01) |
| *G08B 17/113* | (2006.01) |
| *G08B 29/14* | (2006.01) |

(52) U.S. Cl.
CPC ......... *G01D 11/245* (2013.01); *G01N 33/004* (2013.01); *G01N 33/0073* (2013.01); *G08B 17/113* (2013.01); *G08B 29/145* (2013.01); *Y02A 50/243* (2018.01)

(58) Field of Classification Search
CPC .... G01D 11/245; G08B 17/10; G08B 17/113; G08B 29/145

USPC .......................................................... 340/628
See application file for complete search history.

(56) References Cited

U.S. PATENT DOCUMENTS

| | | | |
|---|---|---|---|
| 5,289,165 A | | 2/1994 | Belin |
| 5,555,455 A | * | 9/1996 | McGinley ............ G08B 17/113 340/584 |
| 5,594,422 A | | 1/1997 | Huey, Jr. et al. |
| 7,504,960 B2 | | 3/2009 | McGrath |
| 8,541,124 B2 | | 9/2013 | Lenkszus |
| 2005/0099312 A1 | | 5/2005 | Blanche |

* cited by examiner

*Primary Examiner* — John A Tweel, Jr.
(74) *Attorney, Agent, or Firm* — Global Intellectual Property Agency, LLC; Daniel Boudwin

(57) ABSTRACT

An interior sensor assembly is provided that comprises a first sensor housing that is mounted to a first interior surface, and a second battery housing that is mounted to a second interior surface. The battery housing and the sensor housings are electrically connected by way of a wired connection therebetween, and the battery housing is independently mountable relative to the sensor housing. In use, the sensor housing is mounted in an ideal location for detecting smoke, heat, carbon monoxide, or the like, while the battery housing is mounted in a convenient location such that a user has ready access to check and replace the battery when necessary. The battery housing comprises a lid, and optionally comprises a local circuit that supports an additional sensor or test circuit. The battery housing and the sensor housing may be secured to studs within an interior wall, or optionally using drywall tabs.

17 Claims, 4 Drawing Sheets

INTERIOR SENSOR WITH A REMOTE POWER SOURCE

CROSS REFERENCE TO RELATED APPLICATION

This application claims the benefit of U.S. Provisional Application No. 62/089,317 filed on Dec. 9, 2014. The above identified patent application is herein incorporated by reference in its entirety to provide continuity of disclosure.

BACKGROUND OF THE INVENTION

Field of the Invention

The present invention relates to residential and commercial indoor detectors, and more particularly to power source maintenance thereof. Specifically, the present invention relates to smoke, carbon monoxide, and other indoor detectors, whereby the detector includes a specific sensor and a remote battery power source is provided that affords easy replacement of the power source when necessary.

Most interior detectors are located along a ceiling surface, making it nearly difficult to reach and to change the battery thereof without climbing a ladder or stepstool. Climbing a ladder to access the detector may be acceptable for some; however this option is dangerous for many. As a result, many people do not regularly check or maintain the batteries of their interior detectors, which can cause the detectors to cease operation over time. This can be even more dangerous, and can result in the loss of life in case of an event in which the detector was designed to sense and warn the home occupants. Additionally, property management companies can get fined if tenants do not replace their detector batteries. At the same time, it can be time consuming and expensive for these companies to send technicians to simply change a battery. Therefore, a need exists for an easier way to replace smoke alarm batteries.

Most smoke, fire, and carbon monoxide detectors are battery-powered devices that include a sensor and an interior battery power source. The sensor is disposed along an interior surface, and the user must access the sensor location in order to service the device. The present invention provides an independent power source for an interior sensor, whereby the sensor can be deployed in an ideal location within a home, and a separate battery housing is provided that can be mounted in a more convenient location for checking and changing the battery power supply. The battery housing and the sensor housing are independently mounted, but electrically connected by way of a wired electrical connection. In use, the two housings can be installed during construction of the home; however, installation is contemplated after drywall is installed and the home is completed.

SUMMARY OF THE INVENTION

The following summary is intended solely for the benefit of the reader and is not intended to be limiting in any way. The present invention provides a new interior sensor, wherein the same can be utilized for detecting smoke, heat, or other emergency events, while an independently-mounted battery housing provides power to the device and improved access to the battery of the sensor.

It is therefore an object of the present invention to provide a new and improved sensor device that has all of the advantages of the prior art and none of the disadvantages.

It is another object of the present invention to provide a sensor device that comprises a sensor housing having a base adapted to be mounted along a first interior surface, and a battery housing mounting along a second interior surface. The battery housing and the sensor housing are electrically connected by way of a wired electrical connection extending behind the interior surfaces and between the two housings.

Another object of the present invention is to provide a sensor housing supporting an alarm horn, a control circuit, and a sensor assembly for detecting one of smoke, heat, or carbon monoxide. The control circuit that is adapted to receive inputs from the sensor assembly and energize the alarm horn when an event is detected.

Another object of the present invention is to provide a sensor device with a battery housing having sidewalls, an interior, and a battery power source disposed within the interior. The battery housing comprises an opening for accessing the interior and the battery power source, whereby the opening being operatively covered by a lid.

Another object of the present invention is to provide a sensor device wherein the battery housing includes a battery terminal connector at a first end of the wired electrical connection, whereby the first end is disposed within the interior of the battery housing for operatively connecting and removing the battery power source from the wired electrical connection.

Another object of the present invention is to provide a sensor device wherein the sensor housing is mounted along a ceiling surface, and the battery housing is mounted to an adjacent, vertical wall.

Another object of the present invention is to provide a sensor device in which the sensor housing further comprises a sensing chamber for detecting smoke, heat, or carbon monoxide.

Another object of the present invention is to provide a sensor device wherein a second wired electrical connection is electrically connected to the first wired electrical connection, and the second wired electrical connection extends into the lid of the battery housing to electrically connect the battery power source to a battery test circuit.

Another object of the present invention is to provide a sensor device wherein a second wired electrical connection is electrically connected to the first wired electrical connection, and the second wired electrical connection extends into the lid of the battery housing to electrically connect the battery power source to a second sensor.

Another object of the present invention is to provide a sensor device wherein a second wired electrical connection is electrically connected to the first wired electrical connection by way of an electrical junction in the battery housing.

Another object of the present invention is to provide a sensor device wherein the sidewalls of the battery housing are disposed through the second interior surface such that the interior of the battery housing is substantially behind the second interior surface, and the opening of the battery housing is disposed substantially in plane with an outer surface of the second interior surface.

Another object of the present invention is to provide a sensor device wherein the battery housing further comprises drywall tabs that are rotatable from the sidewalls of the battery housing. The opening of the battery housing may further comprise an outer lip that is adapted to be pressed against the outer surface of the second interior surface, whereby the second interior surface is sandwiched between the drywall tabs and the outer lip when the drywall tabs are rotated outward from the sidewalls of the battery housing.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1A:
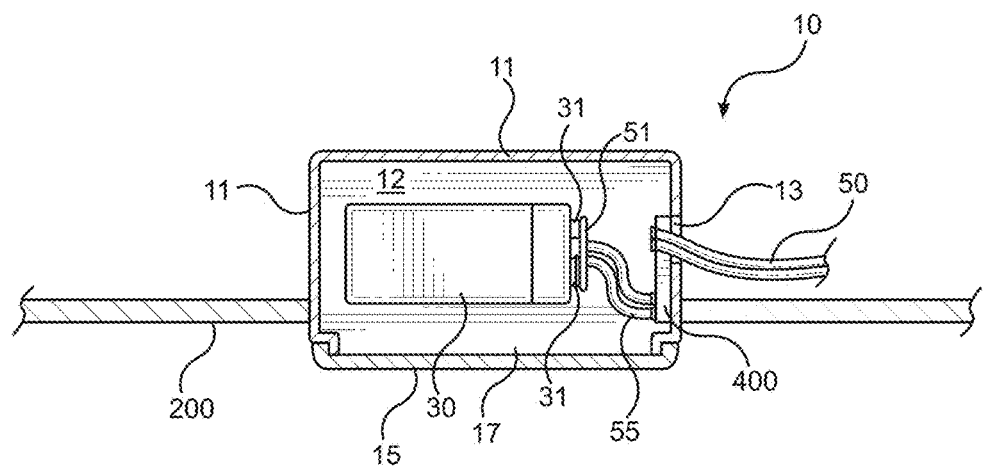
FIG. 1A shows an overhead cross section view of the battery housing of the present invention installed behind the first interior wall surface.

Reference is made herein to the attached drawings. Like reference numerals are used throughout the drawings to depict like or similar elements of the sensor device of the present invention. For the purposes of presenting a brief and clear description of the present invention, the preferred embodiment will be discussed as used for providing improved access to the battery power source of an interior detector or alarm. The figures are intended for representative purposes only and should not be considered to be limiting in any respect.

Figure 1B:
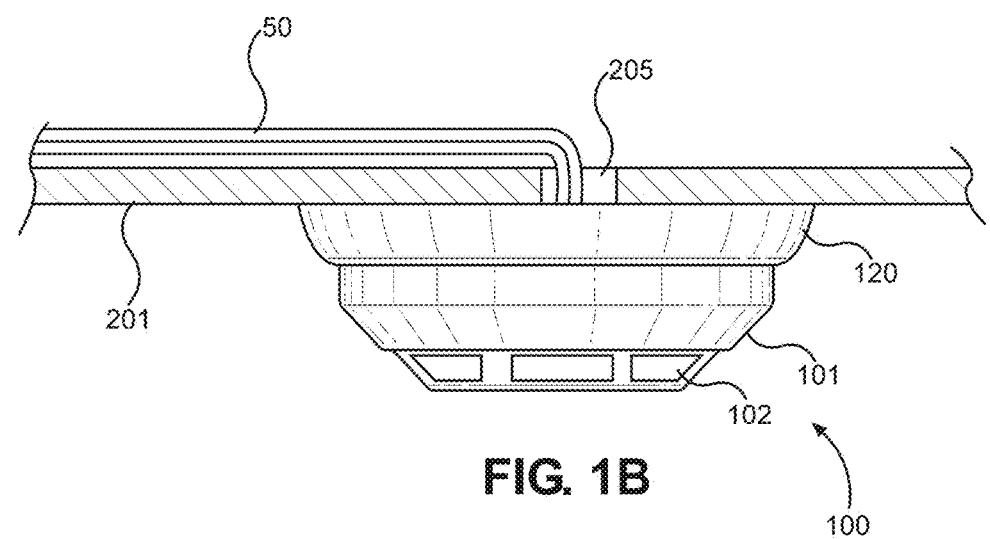
FIG. 1B shows a side view of the sensor housing of the present invention installed along the second interior wall surface.

Referring now to FIGS. 1A and 1B, there are shown views of the battery housing 10 and the sensor housing 100 of the present invention. The battery housing 10 is a wall-mounted support for a battery power source 30, which is connected to a sensor control circuit in the sensor housing 100 by way of a wired connection 50. The battery housing 10 is adapted to support a battery 30 that powers the control circuit within the sensor housing 100, whereby the two housings are separately located within the interior of a home. In this way, the sensor housing 100 may be installed in an ideal location for its operation, and the battery housing 10 may be mounted closer to the ground, and along a wall that affords ready access to a user without using a ladder or stepstool to access the battery 30 thereof.

The battery housing 10 supports a battery 30 and comprises sidewalls 11, an interior 17, a lower surface 12, and a lid 15. The battery housing 10 is adapted to be mounted within an interior wall surface 200, whereby the interior of the housing 10 is within the wall or along the wall 200, and the user can access the interior of the housing 10 by way of the lid 15. The sensor housing 100 is similarly adapted to be mounted to an interior wall surface 201. The sensor housing 100 is mounted to a first interior surface 201, and the battery housing 10 is mounted to a second interior surface 200. In this way, the sensor housing 100 and the battery housing 10 are not collocated, and the battery 30 can be positioned in a convenient location for battery replacement and testing.

Referring to FIG. 1A, the battery 30 is disposed within the battery housing 10 and is electrically connected to the sensor housing by way of a wired electrical connection 50. The wired electrical connection 50 extends from within the interior 17 of the battery housing 10 and through an aperture 13 in one of the sidewalls 11 thereof. The wired electrical connection 50 includes a length sufficient to connect the battery power source 30 within the battery housing 10 to a control circuit of the sensor housing 100. The wired electrical connection 50 extends from the battery housing 10 and is preferably routed behind the second interior surface 200 and the first interior surface supporting the sensor housing. The wired electrical connection 50 then is routed through the base 120 of the sensor housing 100 and to the control circuit, as shown in FIG. 1B.

The wired electrical connection comprises a battery terminal connector 51 at a first end, which is adapted to connect to the terminals 31 of the battery 30. The terminal connector 51 is disposed within the interior 17 of the battery housing 10 for operatively connecting and removing the battery power source 30 from the wired electrical connection 50. The wired electrical connection 50 may directly extend from the battery terminal connector 51 to the sensor housing. Alternatively, the battery housing may comprise an electrical junction 400, in which the battery terminal connector 51 is connected by a lead wire 55 to the junction 400. The wired electrical connection 50 extending between the housings is also connected to the junction 400, whereby electrical power is provided through the junction 400 at two or more junction connection points.

Figure 2:
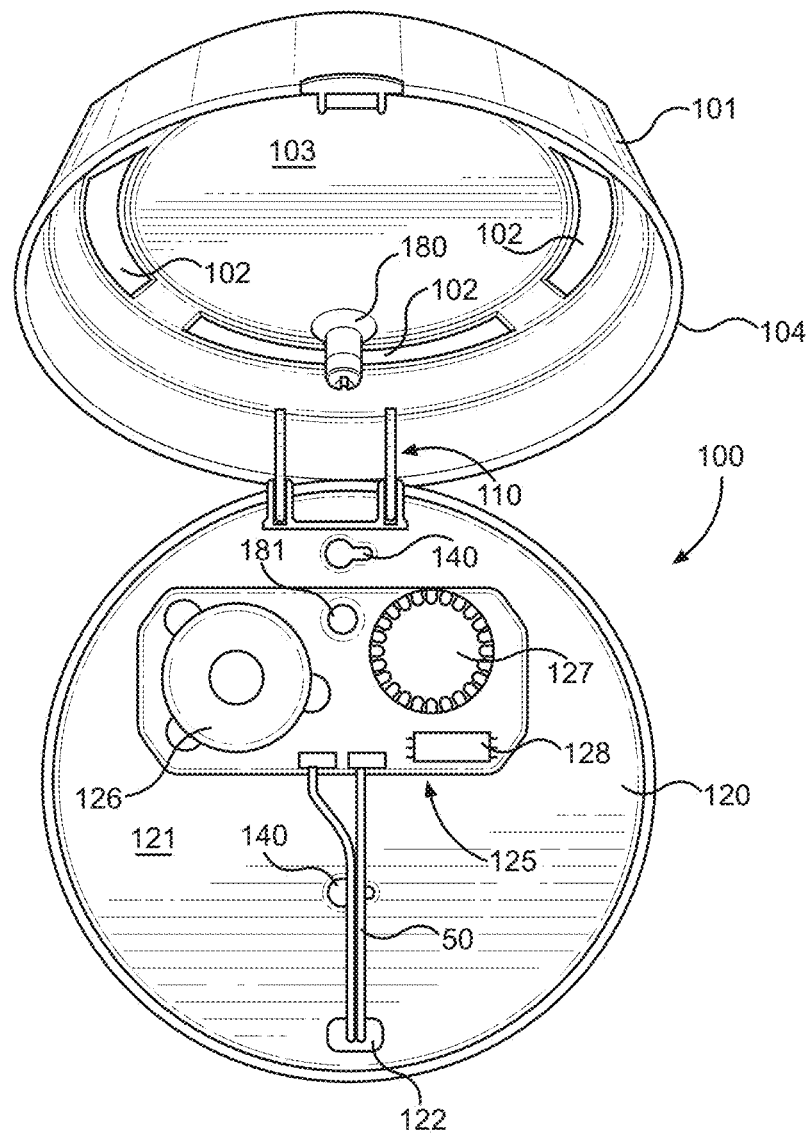
FIG. 2 shows a view of the internal components of the sensor housing, whereby the lid of the sensor housing is opened.

Referring now to FIGS. 1B and 2, there are shown views of the sensor housing 100 of the present invention. The sensor housing 100 supports an alarm and a detector that are used to first detect an emergency event, and then sound an alarm. The emergency event may include smoke, heat, or carbon monoxide within the interior of a home, and the alarm may include audible alarms and other alarm signals (e.g. radio signals to remote receivers, etc.). The sensor housing includes a base 120 that is adapted to be mounted along the first interior surface 201. This generally is a ceiling surface or a vertical wall surface. The sensor housing 100 supports an alarm horn 126, a control circuit 128, and a sensor assembly 127. The alarm horn 126 is an audible alarm that sounds when the control circuit 128 directs the horn 126 to activate. The control circuit 128 is an analog circuit or microprocessor that receives inputs from the sensor assembly 127 and energizes the alarm horn 126 when an event is detected. The sensor assembly 127 comprises a sensing chamber or similar electromechanical assembly that is designed to detect a specific event. This includes the presence of smoke, heat, or carbon monoxide. It is contemplated that the sensor assembly 127 senses one or more events, and is not limited to sensing smoke, heat, or carbon monoxide.

The sensor housing 100 secures to the second interior surface 201 preferably using fasteners through fastener apertures 140 in the base 120 of the housing. The wired electrical connection 50 extends from the battery housing and enters the sensor housing 100 through a wire aperture 205 through the wall 201, and through an opening 122 in the base 120 of the sensor housing 100. The sensor housing further comprises a lid 101, whereby the lid 101 is hinged 110 to the base 120 and may include apertures 102 that permit the sensor assembly to detect the presence of heat, smoke, or carbon monoxide in the air. Along the top surface 103 of the housing lid 101 may be a test button 180. The test button 180 can be used to manually activate the alarm horn 126 when the user is testing the connectivity of the battery and the control circuit 128. The test button 180 extends through the lid 101 and makes contact with a switch 181 on the control circuit board 125, the control circuit board 125 being disposed along the interior surface 121 of the base 120. When the button 180 is pressed, the switch 181 is depressed and activated, thereby activating the alarm horn 126 if electrical power is being received from the remote battery.

Figure 3:
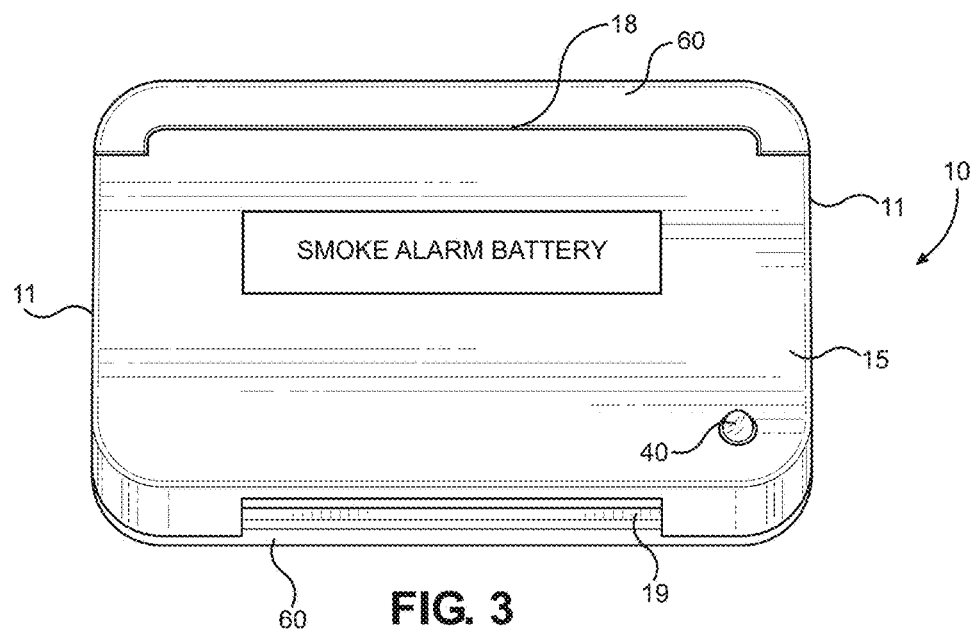
FIG. 3 shows an exterior view of the battery housing of the present invention in the first interior wall surface, whereby the lid of the housing is closed.
Figure 4:
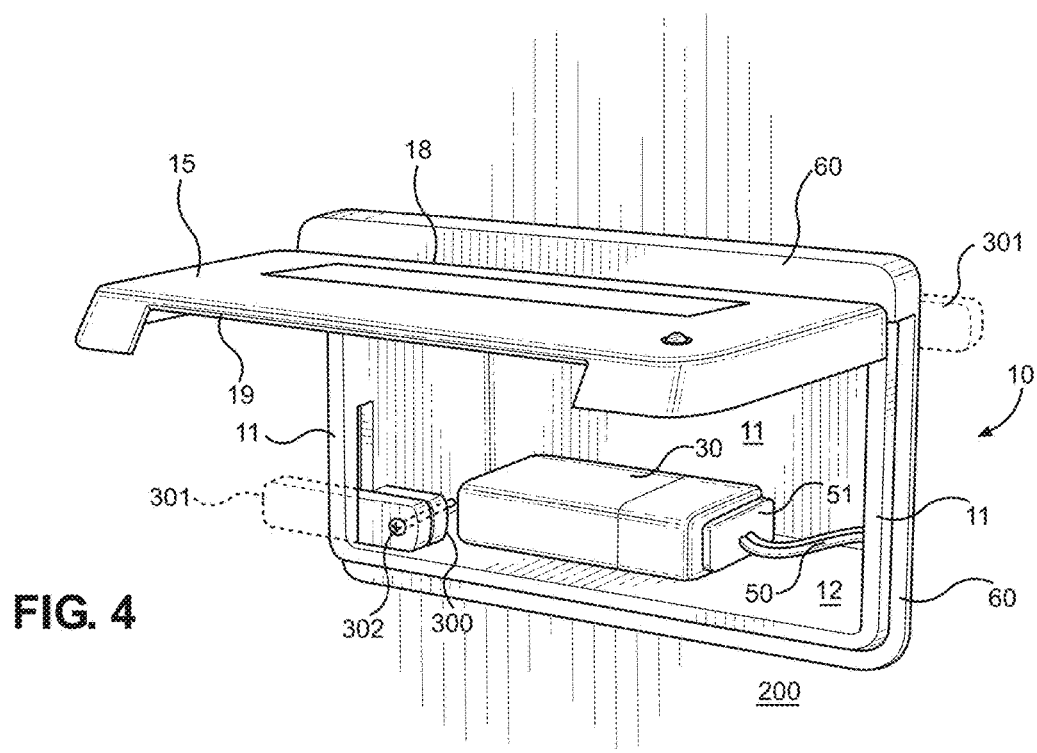
FIG. 4 shows another view of the battery housing of the present invention with the lid of the housing in an open position and a battery disposed therein.
Figure 5:
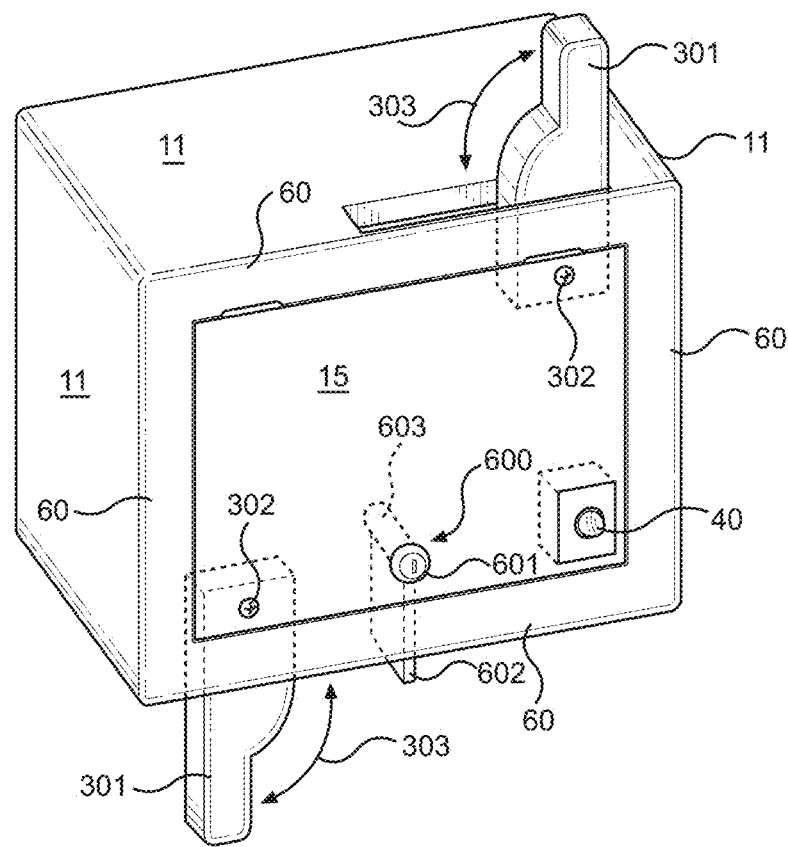
FIG. 5 shows an embodiment of the battery housing, and particularly the drywall tabs that extend from the sidewalls thereof to secure the battery housing to an interior surface.

Referring now to FIGS. 3-5, there are shown views of the battery housing 10 of the present invention, whereby the housing 10 is mounted along an interior wall. The battery housing 10 includes a housing interior, sidewalls 11, a lower surface 12, and a lid 15. A battery 30 is adapted to be supported within the housing interior, and a wired electrical connection 50 connects the battery 30 to the sensor housing. It is preferred that the battery housing 10 be disposed within a wall surface 200 in a location that allows a user to readily access the interior of the housing to replace the battery 30 when needed. This eliminates the need for stepstools or ladders when accessing the power source of an interior sensor. The battery housing 10 may be mounted along a first surface 200, while the sensor housing may be mounted along a second interior surface. The surfaces may be the same, whereby the battery housing 10 is lower on the wall than the sensor housing. Alternatively, the sensor housing may be mounted along an adjacent surface, such as the ceiling.

The battery housing 10 may also have a peripheral lip 60 along the perimeter of the housing opening. The lip 60 is adapted to abut against the interior surface of the wall 200, while the interior of the housing is positioned completely within the wall surface. Alternatively, the rear sidewall 11 of the housing may be supported against the wall surface 200, and the housing may be cantilevered from the wall 200. In one preferred configuration, the sidewalls 11 of the housing 10 are disposed within the wall surface 200, the lip 60 bears against the outer surface thereof, and drywall tabs 301 secure the housing to the wall surface. In yet another configuration, the housing may include fasteners for securing the housing sidewalls 11 to a stud behind the wall surface 200. Once installed, a battery 30 is placed within the housing interior, and the wired electrical connection 50 is connected thereto using the battery terminal connector 51. This provides electrical power to the remotely-installed sensor housing.

The lid 15 of the housing 10 secures over the opening thereof, thereby shrouding the interior of the housing. The lid 15 is pivotably connected to the housing by way of a hinge 18, thereby allowing the lid 15 to pivot away from the housing when accessing the battery therein. The lid 15 may further comprise a pull tab or handle recess 19 along one edge to facilitate opening thereof.

In one embodiment, the lid further comprises an electrical assembly along its surface. A second wired connection, branching from the first wired connection, provides power to the electrical assembly in the lid 15. Different embodiments are contemplated, including a light source 40 within the lid 15, an additional sensor, or a test circuit button. The light source 40 energizes when the battery is connected to the first wired connection 50 and electrical power is being delivered to the second wired circuit. Similarly, the additional sensor receives power from the second wired connection, and further connects to the control circuit of the housing to sound the alarm horn when the additional sensor detects an event. Finally, the alarm test button within lid 15 provides a means to test the electrical connectivity between the housings, whereby the test button connects to the control circuit of the housing to sound the alarm horn when the test button is activated.

Referring to FIGS. 4 and 5, the drywall tabs 301 of the battery housing are illustrated. In this embodiment of the battery housing 10, drywall tabs 301 are rotatably supported by the sidewalls of the housing. The tabs 301 are utilized in conjunction with the lip 60 of the housing to sandwich the drywall of an interior surface 200 between the tab 301 and the lip 60. The drywall tabs 301 are pivotably mounted to the sidewalls 11 of the housing, and rotate 303 between a stowed position against the sidewalls 11 and a deployed state, extending outward from the sidewalls 11 of the housing. FIGS. 4 and 5 illustrate the tabs 301 in their deployed state. A fastener 302 secures the tabs 301 to the sidewalls, or to an interior tab 300 along the sidewalls. When the fastener 302 is rotated, the tabs rotate accordingly.

Optionally provided and for added security, a lock 600 may be provided between the lid 15 and the housing 10. A lock prevents unauthorized access into the housing interior, and thus prevents individuals from opening the lid 15 and removing the battery therein. This is particularly useful when the housing 10 is deployed in a public space, such as in the hallway of an apartment building or in common areas. This prevents removal of the battery except for maintenance personnel and authorized users, thereby preventing unwanted deactivation of the detector and theft of the battery. The lock 600 may take on several forms. In one embodiment, the lock comprises a lock tumbler 603, a key slot 601, and a tab 602 that engages an aperture in the housing sidewalls 11. The tab 602 prevents the lid 15 from opening when deployed in a locked state, while the tumbler 603 limits the operation of the lock by preventing movement except when a specific key is inserted into the tumbler.

Figure 6:
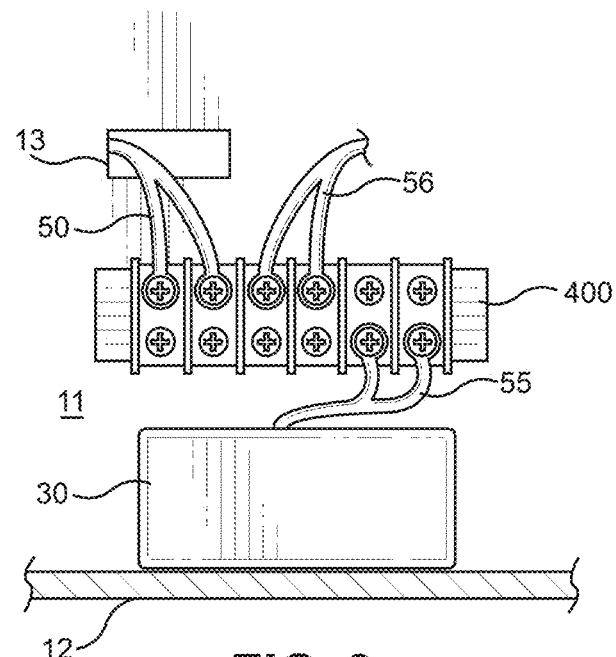
FIG. 6 shows an end view of the battery within the battery housing, and the wired connections between the battery, the sensor housing, and the embodiment of the battery housing lid that comprises an additional sensor or test circuit.

Referring now to FIG. 6, there is shown a view of the electrical junction 400 of the present invention. The electrical junction 400 is an embodiment that electrically connects the battery lead wire 55 to the wired connection 50 between the housings. The junction 400 furthermore permits additional wires to be electrically connected to the battery 30. For the embodiment of the battery housing lid requiring electrical power, a second wired electrical connection 56 connects to the junction 400 and routes power to the lid. The second wired electrical connection 56 connects the optional light source, battery test circuit, or the additional sensor in the lid. The electrical junction allows wires to be electrically connected and receive power from a common power source: the battery 30 within the housing interior. The battery 30 is supported along the base 12 of the housing, while the junction 400 may be supported along one of the sidewalls 11 thereof. The wired connection 50 between the housings extends from the junction 400 and exits the housing through an aperture 13 through one of the sidewalls 11 thereof.

Overall, the present invention offers a safer and more convenient system and method to change the battery of an interior sensor. The system relocates the battery of the system to remotely-located wall, independent of the location of the sensor housing. This eliminates the need to climb a stepstool or ladder in order to change the battery of a smoke or fire alarm. The present invention, therefore, prevents injuries associated with falling from a stepstool or ladder. Furthermore, use of the present invention saves time and money for property management companies and their technicians.

Accompanying the system is a method. The method includes a method of providing a remote power source for an interior sensor, comprising the steps of (1) providing a sensor housing having a base adapted to be mounted along a first interior surface; (2) providing a battery housing mounting along a second interior surface; and (3) providing a wired electrical connection that extends from within the interior of the battery housing and through one of the sidewalls thereof. The sensor housing supports an alarm horn, a control circuit, and a sensor assembly, while the control circuit is adapted to receive inputs from the sensor assembly and energize the alarm horn when an event is detected. The battery housing comprises sidewalls, an interior, and a battery power source disposed within the interior. Additionally, the battery housing further comprises an opening for accessing the interior and the battery power source, the opening being operatively covered by a lid. The wired electrical connection has a length sufficient to connect the battery power source within the battery housing to the control circuit of the sensor housing. Furthermore, the wired electrical connection is adapted to extend from the battery housing, behind the second interior surface and the first interior surface, and through the base of the sensor housing to the control circuit. Finally, the wired electrical connection further comprises a battery terminal connector at a first end, the first end being disposed within the interior of the battery housing for operatively connecting and removing the battery power source to the battery terminal connector.

Alternatively, the present invention provides a method of providing a remote power source for an interior sensor, comprising the steps of (1) securing a sensor housing having a base along a first interior surface; (2) securing a battery housing mounting along a second interior surface; (3) connecting the sensor housing to the battery housing using a wired electrical connection that extends from within the interior of the battery housing and through one of the sidewalls thereof; and (4) routing the wired electrical connection from the battery housing, behind the second interior surface and the first interior surface, and through the base of the sensor housing to the control circuit. As with the above, the sensor housing supports an alarm horn, a control circuit, and a sensor assembly, and the control circuit is adapted to receive inputs from the sensor assembly and energize the alarm horn when an event is detected. The battery housing comprises sidewalls, an interior, and a battery power source disposed within the interior. Additionally, the battery housing comprises an opening for accessing the interior and the battery power source, the opening being operatively covered by a lid. The wired electrical connection comprises a length sufficient to connect the battery power source within the battery housing to the control circuit of the sensor housing. Finally, the wired electrical connection further comprises a battery terminal connector at a first end, the first end being disposed within the interior of the battery housing for operatively connecting and removing the battery power source to the battery terminal connector.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An interior sensor with a remote power source, comprising:
   a sensor housing having a base adapted to be mounted along a first interior surface;
   the sensor housing supporting an alarm horn, a control circuit, and a sensor assembly;
   the control circuit being adapted to receive inputs from the sensor assembly and energize the alarm horn when an event is detected;
   a battery housing mounting along a second interior surface;
   the battery housing having sidewalls, an interior, and a battery power source disposed within the interior;
   the battery housing having an opening for accessing the interior and the battery power source, the opening being operatively covered by a lid;
   a wired electrical connection extending from within the interior of the battery housing and through one of the sidewalls thereof;
   the wired electrical connection having a length sufficient to connect the battery power source within the battery housing to the control circuit of the sensor housing;
   the wired electrical connection extending from the battery housing and routing behind the second interior surface and the first interior surface, and then through the base of the sensor housing to the control circuit;
   the wired electrical connection having a battery terminal connector at a first end, the first end being disposed within the interior of the battery housing for operatively connecting and removing the battery power source to the battery terminal connector;
   a second wired electrical connection electrically connected to the first wired electrical connection;
   the second wired electrical connection extending into the lid and electrically connecting the battery power source to a second sensor disposed within the lid.

2. The interior sensor with a remote power source of claim 1, wherein the first interior surface is a ceiling surface, and the second interior surface is an adjacent, vertical wall.

3. The interior sensor with a remote power source of claim 1, wherein the sensor housing further comprises a sensing chamber for detecting smoke, heat, or carbon monoxide.

4. The interior sensor with a remote power source of claim 1, further comprising:
   a second wired electrical connection electrically connected to the first wired electrical connection;
   the second wired electrical connection extending into the lid and electrically connecting the battery power source to a battery test circuit.

5. The interior sensor with a remote power source of claim 4, wherein the battery test circuit further comprises a light source that indicates the power remaining in the battery power source, the light source being disposed along an exterior of the lid.

6. The interior sensor with a remote power source of claim 1, wherein:
the sidewalls of the battery housing are disposed through the second interior surface such that the interior of the battery housing is substantially behind the second interior surface and the opening is disposed substantially in plane with an outer surface of the second interior surface.

7. The interior sensor with a remote power source of claim 6, wherein:
the battery housing further comprises drywall tabs that are rotatable from the sidewalls of the battery housing;
the opening of the battery housing further comprising an outer lip that is adapted to be pressed against the outer surface of the second interior surface;
the second interior surface being sandwiched between the drywall tabs and the outer lip when the drywall tabs are rotated outward from the sidewalls of the battery housing.

8. A method of providing a remote power source for an interior sensor, comprising the steps of:
providing a sensor housing having a base adapted to be mounted along a first interior surface;
the sensor housing supporting an alarm horn, a control circuit, and a sensor assembly;
the control circuit being adapted to receive inputs from the sensor assembly and energize the alarm horn when an event is detected;
providing a battery housing mounting along a second interior surface;
the battery housing having sidewalls, an interior, and a battery power source disposed within the interior;
the battery housing having an opening for accessing the interior and the battery power source, the opening being operatively covered by a lid;
providing a wired electrical connection that extends from within the interior of the battery housing and through one of the sidewalls thereof;
the wired electrical connection having a length sufficient to connect the battery power source within the battery housing to the control circuit of the sensor housing;
the wired electrical connection adapted to extend from the battery housing, behind the second interior surface and the first interior surface, and then through the base of the sensor housing to the control circuit;
the wired electrical connection having a battery terminal connector at a first end, the first end being disposed within the interior of the battery housing for operatively connecting and removing the battery power source to the battery terminal connector;
a second wired electrical connection electrically connected to the first wired electrical connection;
the second wired electrical connection extending into the lid and electrically connecting the battery power source to a second sensor disposed within the lid.

9. The method of claim 8, wherein the sensor housing further comprises a sensing chamber for detecting smoke, heat, or carbon monoxide.

10. The method of claim 8, further comprising:
a second wired electrical connection electrically connected to the first wired electrical connection; the second wired electrical connection extending into the lid and electrically connecting the battery power source to a battery test circuit.

11. The method of claim 10, wherein the battery test circuit further comprises a light source that indicates the power remaining in the battery power source, the light source being disposed along an exterior of the lid.

12. The method of claim 8, wherein:
the sidewalls of the battery housing are disposed through the second interior surface such that the interior of the battery housing is substantially behind the second interior surface and the opening is disposed substantially in plane with an outer surface of the second interior surface.

13. The method of claim 12, wherein:
the battery housing further comprises drywall tabs that are rotatable from the sidewalls of the battery housing;
the opening of the battery housing further comprising an outer lip that is adapted to be pressed against the outer surface of the second interior surface;
the second interior surface being sandwiched between the drywall tabs and the outer lip when the drywall tabs are rotated outward from the sidewalls of the battery housing.

14. A method of providing a remote power source for an interior sensor, comprising the steps of:
securing a sensor housing having a base along a first interior surface;
the sensor housing supporting an alarm horn, a control circuit, and a sensor assembly;
the control circuit being adapted to receive inputs from the sensor assembly and energize the alarm horn when an event is detected;
securing a battery housing mounting along a second interior surface;
the battery housing having sidewalls, an interior, and a battery power source disposed within the interior;
the battery housing having an opening for accessing the interior and the battery power source, the opening being operatively covered by a lid;
connecting the sensor housing to the battery housing using a wired electrical connection that extends from within the interior of the battery housing and through one of the sidewalls thereof;
the wired electrical connection having a length sufficient to connect the battery power source within the battery housing to the control circuit of the sensor housing;
routing the wired electrical connection from the battery housing, behind the second interior surface and the first interior surface, and through the base of the sensor housing to the control circuit;
the wired electrical connection having a battery terminal connector at a first end, the first end being disposed within the interior of the battery housing for operatively connecting and removing the battery power source to the battery terminal connector;
a second wired electrical connection electrically connected to the first wired electrical connection;
the second wired electrical connection extending into the lid and electrically connecting the battery power source to a second sensor disposed within the lid.

15. The method of claim 14, wherein the sensor housing further comprises a sensing chamber for detecting smoke, heat, or carbon monoxide.

16. The method of claim 14, further comprising:
a second wired electrical connection electrically connected to the first wired electrical connection;
the second wired electrical connection extending into the lid and electrically connecting the battery power source to a battery test circuit.

17. The method of claim 14, wherein: the sidewalls of the battery housing are disposed through the second interior surface such that the interior of the battery housing is substantially behind the second interior surface and the opening is disposed substantially in plane with an outer surface of the second interior surface.

\* \* \* \* \*